United States Patent [19]

Johnson

[11] 4,182,334

[45] * Jan. 8, 1980

[54] PERINEAL SHIELD AND DISCHARGE CONTAINMENT DEVICE

[75] Inventor: Russell L. Johnson, Weyauwega, Wis.

[73] Assignee: Kimberly-Clark Corporation, Neenah, Wis.

[ * ] Notice: The portion of the term of this patent subsequent to Jan. 10, 1995, has been disclaimed.

[21] Appl. No.: 857,530

[22] Filed: Dec. 5, 1977

Related U.S. Application Data

[63] Continuation-in-part of Ser. No. 726,964, Sep. 27, 1976, Pat. No. 4,067,336.

[51] Int. Cl.² .............................................. A61F 13/16
[52] U.S. Cl. ...................................... 128/287; 128/284
[58] Field of Search ................... 128/284, 287, 290 R, 128/288, 290 P, 290 B

[56] References Cited

U.S. PATENT DOCUMENTS

| | | | |
|---|---|---|---|
| 2,059,956 | 11/1936 | MacGlashan | 128/284 |
| 2,092,346 | 9/1937 | Arone | 128/284 |
| 2,827,053 | 3/1958 | Gordon | 128/287 |
| 4,067,336 | 1/1978 | Johnson | 128/284 |

Primary Examiner—Robert W. Michell
Assistant Examiner—C. W. Shedd
Attorney, Agent, or Firm—Daniel J. Hanlon, Jr.; William D. Herrick; Howard Olevsky

[57] ABSTRACT

A perineal shield and discharge containment device comprised of a sheet of flexible material adapted for folding along a plurality of pre-established fold lines to provide a folded configuration which will closely conform to the perineal contours of the human body. The pre-established fold lines radiate outward from a common base point interiorly disposed on the longitudinal center-line of the sheet material. When folded as prescribed, the sheet material has an upwardly concave configuration in both transverse and longitudinal directions with the deepest point of the concavity originating at the base point. When the folded sheet material is positioned in contact with the perineum an upstanding anterior portion, comprising the full width of the sheet, covers the pubic area. From the full width anterior portion the folded sheet tapers back to form a narrow isthmus which fits comfortably between the thighs, then diverges outward to form a full width posterior portion which covers the after-parts of the perineum.

30 Claims, 19 Drawing Figures

U.S. Patent  Jan. 8, 1980  Sheet 1 of 5  4,182,334
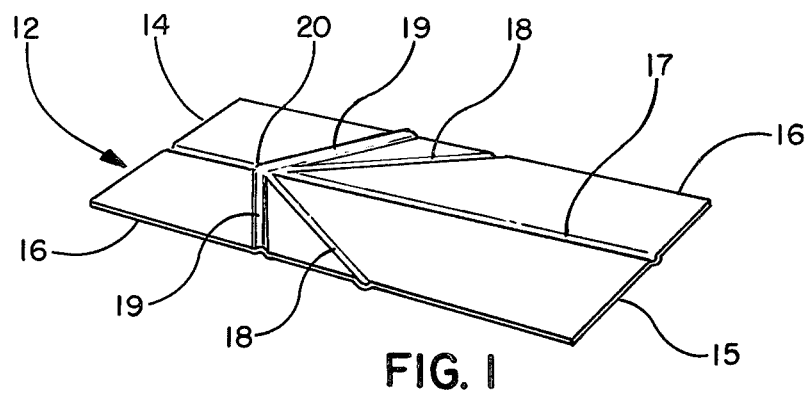
FIG. 1
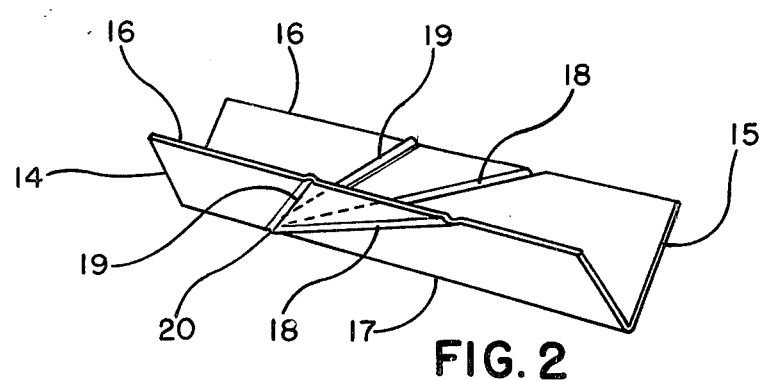
FIG. 2
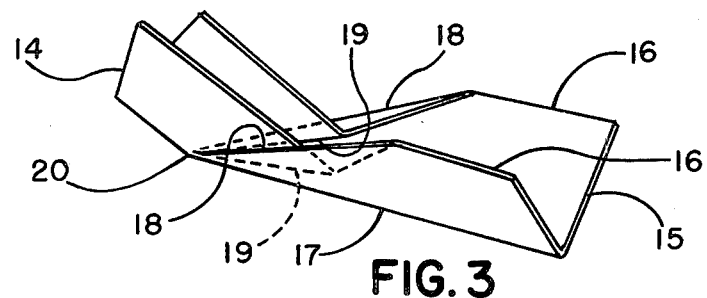
FIG. 3
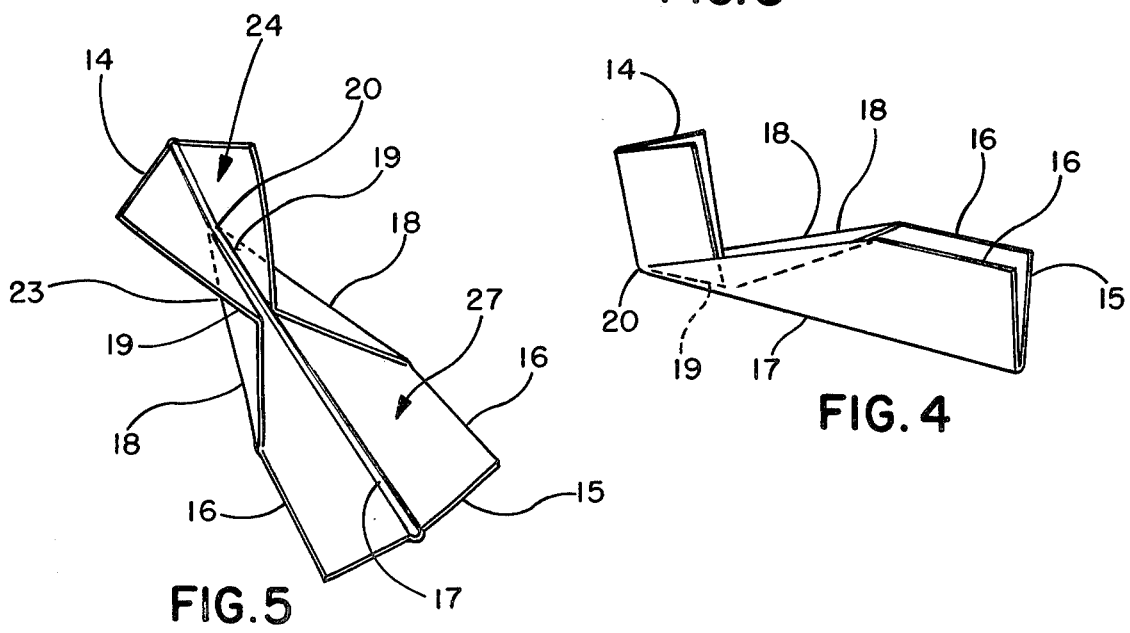
FIG. 5
FIG. 4

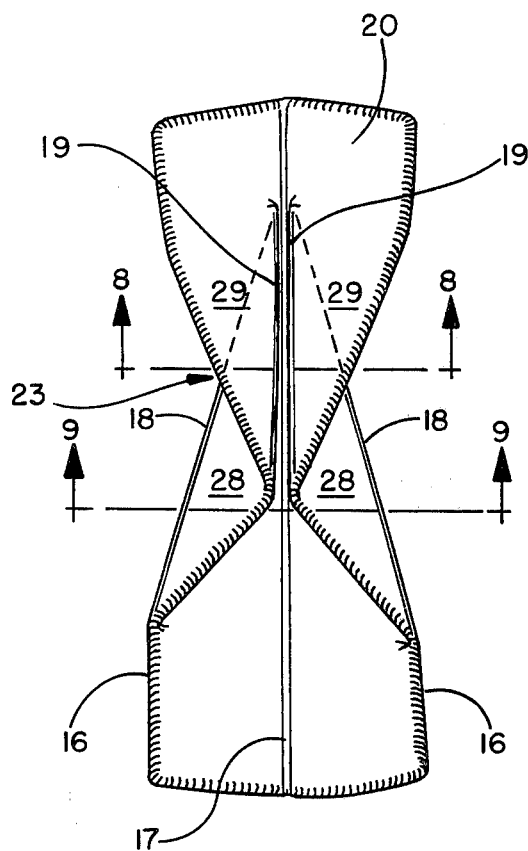
FIG. 6
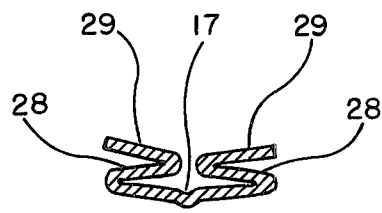
FIG. 8
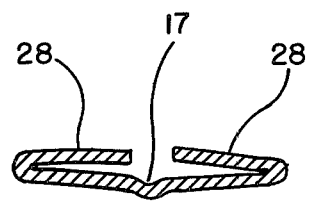
FIG. 9
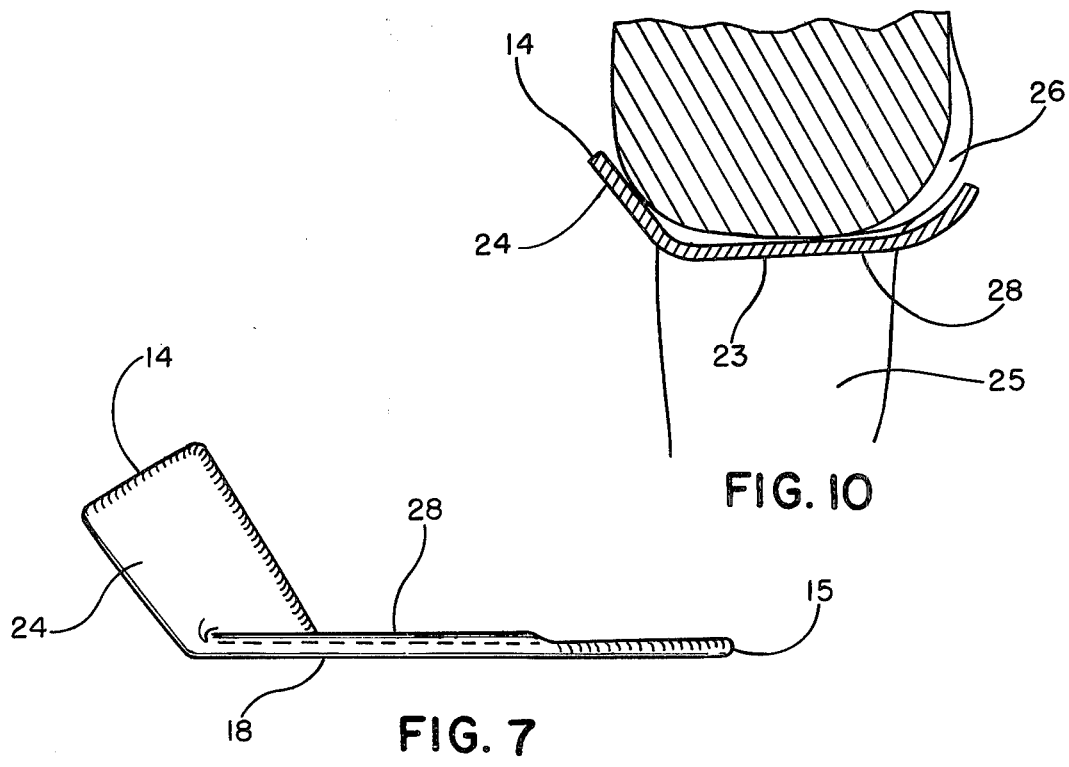
FIG. 7 / FIG. 10

PERINEAL SHIELD AND DISCHARGE CONTAINMENT DEVICE

REFERENCE TO RELATED APPLICATIONS

This is a continuation-in-part of copending application Ser. No. 726,964 filed Sept. 27, 1976, and now U.S. Pat. No. 4,067,336.

BACKGROUND OF THE INVENTION

In the above referenced copending application there is described a perineal shield and discharge containment device comprising a sheet of flexible sheet material adapted for folding along pre-established fold lines which lines are disposed essentially in the same manner as the shield and containment device disclosed herein. The primary difference is that in the present invention the actual folding direction of the sheet along two pair of pre-established rearwardly diverging lines is substantially the reverse of that set forth in the parent application.

In the parent application, the device is described as comprising a sheet of flexible material of generally rectangular form adapted for folding on a set of pre-established fold lines. The sheet material is generally defined by a top body-contacting surface, a bottom surface, a front edge, a back edge, and two side edges. The pre-established fold lines along which the sheet material is folded prior to use comprise: (a) a main fold line centrally and longitudinally disposed along the major axis of the sheet and extending the full length of the sheet; (b) a first pair of rearwardly directed diverging fold lines originating on the main fold line from a common base point spaced inwardly from the front edge of the sheet, and extending to the sheet perimeter; and (c) a second pair of rearwardly directed diverging fold lines disposed between the first pair of diverging lines and the side edges of the sheet, with the second pair of lines also originating at the same common base point on the main fold line as the first set of lines and extending to the sheet perimeter.

The sheet material is adapted for inward folding on the main fold line, outward folding on the first pair of rearwardly diverging lines, and inward folding on the second pair of rearwardly diverging lines.

When the device is folded in accordance with the parent application, the rearward outwardly diverging portion is free to bend, twist and pivot around the base point and to flex up and down along the fold on the longitudinally extending center line whereby the device readily adjusts to body movements.

In the present arrangement, the device is folded inwardly instead of outwardly on the first pair of rearwardly diverging lines and outwardly rather than inwardly on the second pair of rearwardly diverging lines. With this reverse fold arrangement the ability to bend, twist, and pivot around the base point is lost, but the resulting structure is more stable and provides better containment for discharged body fluids. The stable structure of the present arrangement also permits it to be more readily used with its own suspension means so that a snug-fitting supporting undergarment is not necessary during use.

Accordingly, while the reverse fold arrangement of this invention loses some of the advantages of the folded device of the parent application, the present invention has its own distinctive advantages not found in the original concept.

SUMMARY OF THE INVENTION

This invention is directed to a perineal shield and discharge containment device comprised of a sheet of flexible material of generally elongate shape adapted for folding on a set of pre-established fold lines similar to those described in the parent application. The sheet material is generally defined by a top body-contacting surface, a bottom surface, a front edge, a back edge, and two side edges. As in the parent application, the pre-established fold lines along which the sheet material is folded prior to use comprise: (a) a main fold line centrally and longitudinally disposed along the major axis of the sheet and extending the full length of the sheet; (b) a first pair of rearwardly directed diverging fold lines originating on the main fold line from a common base point spaced inwardly from the front edge of the sheet, and extending to the sheet perimeter; and (c) a second pair of rearwardly directed diverging fold lines disposed between the first pair of diverging lines and the side edges of the sheet, with the second pair of lines also originating at the same common base point on the main fold line as the first set of lines and extending to the sheet perimeter.

The sheet material is adapted for inward folding on the main fold line, and then in contrast to the parent application is adapted for inward folding on the first pair of rearwardly diverging lines, and outward folding on the second pair of rearwardly diverging lines.

When folded as prescribed, the sheet material has an upwardly concave or bent configuration in both the transverse and longitudinal directions. The deepest part or greatest depth of the concavity in both directions originates at the above-mentioned common point on the main fold line.

When the folded sheet material is positioned against the perineal area between the thighs it provides an upstanding anterior portion traversing the full width of the sheet which covers and conforms to the pubic area then tapers downward to a narrow isthmus-like section which fits between and conforms to the thighs and due to the folded arrangement is capable of flexing in and out without crushing, and a rearwardly diverging posterior portion which covers and conforms to the remaining perineal area.

The folded structure of this invention may also be provided with supplementary suspension means. In one embodiment, the suspension means comprises a pair of straps, which may be of any flexible material, but preferably are elastic. One end of each strap is attached to a rear corner of the folded sheet with the other end attached to the front corner of the folded sheet on the same side. The straps are adapted to fit around the thighs. Such attachment may be permanent or releasable such as by the provision of fastener means on the strap ends to cooperate with fastener receiving apertures in the folded sheet.

In another embodiment the suspension means comprises a pair of straps each of which is secured along the entire length of one longitudinal edge of the sheet. The two ends of the straps extending beyond each end of the sheet to provide tie means.

Other features, objects and advantages of the invention will become apparent by reference to the accompanying drawings and the detailed description which follows.

BRIEF DESCRIPTION OF THE DRAWINGS

In the drawings:

FIG. 1 is a top perspective view of a rectangular sheet material showing the arrangement of the pre-established fold lines of this invention.

FIGS. 2–4 are perspective views showing the sequential folding of the sheet material along the pre-established fold lines.

FIG. 5 is a top perspective view of the folded sheet material partially reopened and ready for positioning on the body.

FIG. 6 is a top plan view of the folded sheet material of FIG. 5.

FIG. 7 is a side view of the folded sheet material of FIG. 6.

FIG. 8 is a sectional view taken along line 8—8 of FIG. 6.

FIG. 9 is a sectional view taken along line 9—9 of FIG. 6.

FIG. 10 is a partial front-to-back sectional and diagrammatic view of the perineal area of a human body with the FIG. 7 folded sheet material in place.

DETAILED DESCRIPTION OF THE PREFERRED EMBODIMENTS

Figure 11:
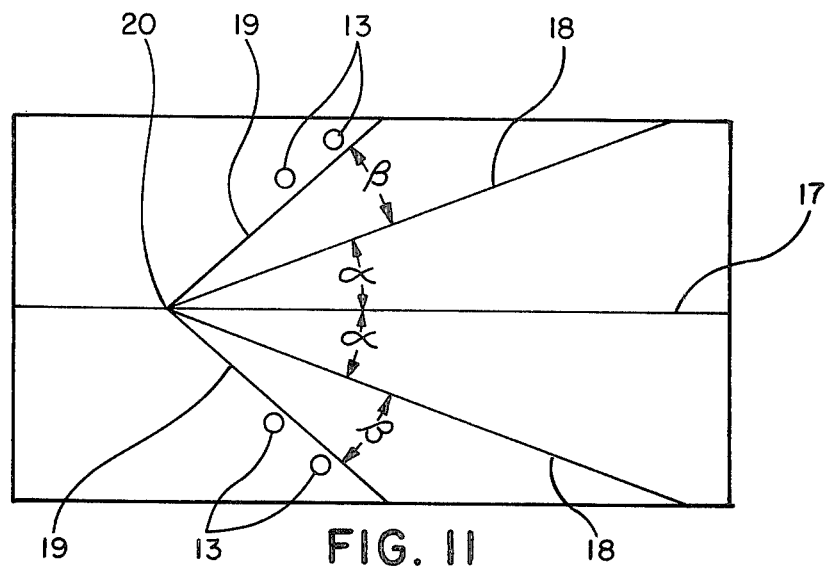
FIG. 11 is a schematic plan view of a rectangular sheet showing an arrangement of fold lines similar to FIG. 1.

FIGS. 1–5 show a series of perspective views of a sheet of flexible material having pre-established fold lines in accordance with the invention, first in its unfolded condition and then followed by sequential folding to a fully folded condition ready for use.

In FIG. 1, an elongate rectangular sheet of material 12 having a front edge 14, a back edge 15 and two side edges 16 is provided with a multiplicity of fold lines including a main fold line 17 centrally and longitudinally disposed along the major axis; a first pair of rearwardly diverging fold lines 18 originating on main fold line 17 from a common base point 20 spaced inwardly from front edge 14 and extending to the sheet perimeter at side edges 16; and a second pair of rearwardly diverging fold lines 19 also originating from base point 20 and disposed in spaced arrangement between the first pair of diverging lines 18 and side edges 16 and terminating at side edges 16.

In the folding sequence, FIG. 2 shows the sheet being folded inwardly on main line 17. FIG. 3 shows the sheet being folded inwardly on the first pair of rearwardly diverging lines 18 and folded back outwardly on the second pair of rearwardly diverging lines 19.

In FIG. 4, the sheet is completely folded.

In FIG. 5, the folded sheet of FIG. 4 has been partially reopened to expose the top surface to illustrate the configuration which the protective device assumes as it is readied for positioning on the perineum. As shown therein the partially opened device has an upstanding frontal portion 24 which comprises the full width of the sheet and angles upward from base point 20, a narrow isthmus-like portion 23 disposed between base point 20 and back edge 15, and an outwardly and rearwardly diverging anterior portion 27 originating at base point 20.

As viewed in this form and in more detail in FIGS. 6–9, the folded device has a concave longitudinal configuration with the base of the concavity at base point 20, being bent upward from that point toward both the front and back, while also having a concave transverse configuration with a base or valley along main fold line 17. The effect is to provide a pouch or cup at the front portion of the device, which bottoms out at base point 20 and functions as a primary containment area.

As shown in FIG. 6 and section FIGS. 8-9, the rearwardly diverging anterior portion of the folded sheet comprises two triangular panels 28 the planar surfaces of which angle transversely inward from side edges 16 along fold lines 18 and have a common forward apex at base point 20. A portion of each of these panels is disposed under another set of triangular panels 29 which angle inward from side edges 16 along fold lines 19 from common apex 20 and overlie panels 28. The advantage of this arrangement is that panels 29, which overlie panels 28, act as a trough to direct discharged fluids into the opening between fold lines 19 and into the pocket formed by the inward fold along lines 18 which in turn define one side of triangular panels 28. The containment capabilities of the device are greatly enhanced by this pocket configuration. Reference to FIG. 10 also shows how well the folded device conforms to the pubic area to aid in the containment capabilities. The upstanding anterior panels 24 (See FIG. 7) is in snug association with the pubic area. The narrow isthmus-like section 23, also referenced in FIGS. 5 and 6, is located centrally of the inner thighs 25 where the thighs are normally in closest proximity, and the triangular anterior panels 28 widen out to the full width which is in contact with the buttocks 26. The fold arrangement which provides the narrow isthmus at the thighs also permits the pad to expand or contract by angular motion of the folds in response to leg pressure without crushing and thereby eliminate one source of discomfort and/or poor fit.

A large variety of shapes and sizes for the basic sheet material, as well as different angular relationships of the rearwardly diverging fold lines are possible without departing from the advantages of this invention. Some of these latter variations are shown in FIGS. 11–16.

Figure 12:
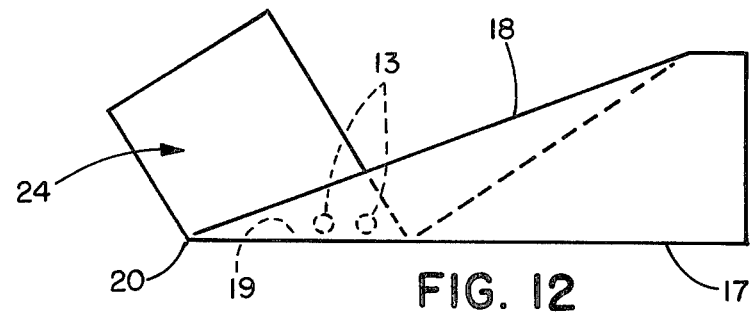
FIG. 12 is a side view of the FIG. 11 material after folding on the pre-established fold lines.

In FIGS. 11–12 the angle α between main fold line 17 and the first pair of outwardly diverging fold lines 18 is equal to angle β between the first pair of outwardly diverging fold lines 18 and the second pair of outwardly diverging fold lines 19.

When this arrangement is folded, fold line 19 lies along main fold line 17.

These figures also show optional adhesive means 13 which can be utilized to maintain the folded configuration in use. In this instance, adhesive means 13 is shown in the form of dots of glue or the like. Other means for securing the device in its folded configuration are also contemplated such as two-sided tape, stitching or the like.

Figure 13:
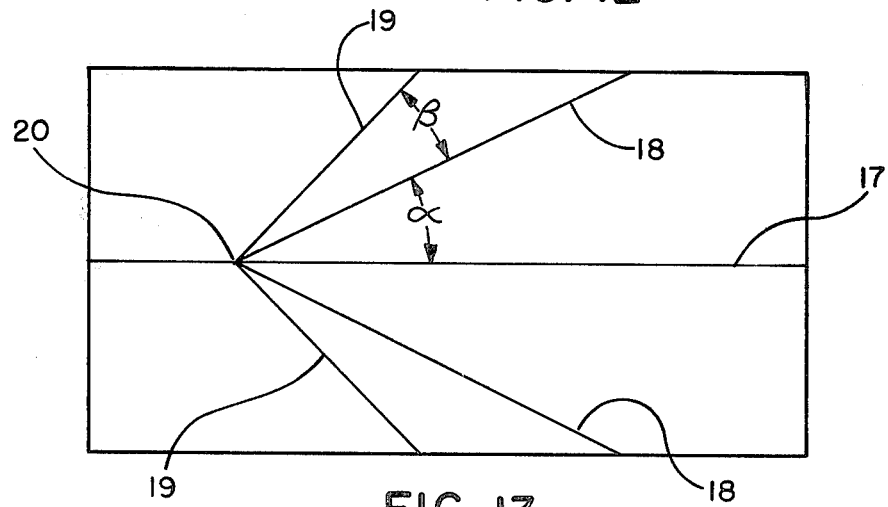
FIG. 13 is a schematic plan view showing another arrangement of fold lines.
Figure 14:
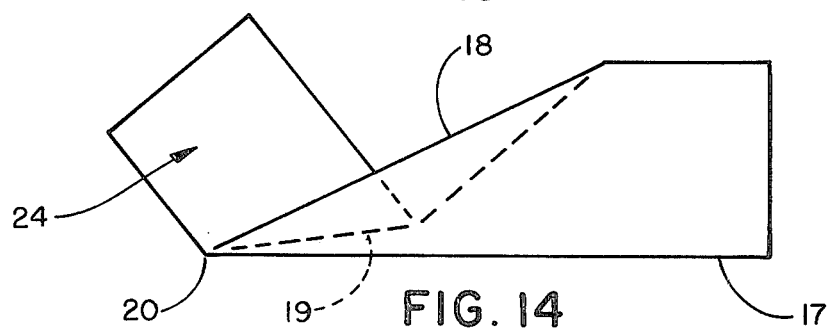
FIG. 14 is a side view of the FIG. 13 embodiment after folding.

In FIGS. 13-14 where angle α is greater than angle β, fold line 19 falls above fold line 17 and the anterior portion 24 of the device moves closer to the horizontal.

Thus by adjusting the relationship between angular disposition of the rearwardly diverging fold lines, one may conveniently adjust the upward angularity of the anterior panel of the device to conform to various body configurations.

As the drawings indicate, angles α and β are always acute angles, whether they are equal or not. A preferred range of angularity is from about 12° to about 30°.

Figure 15:
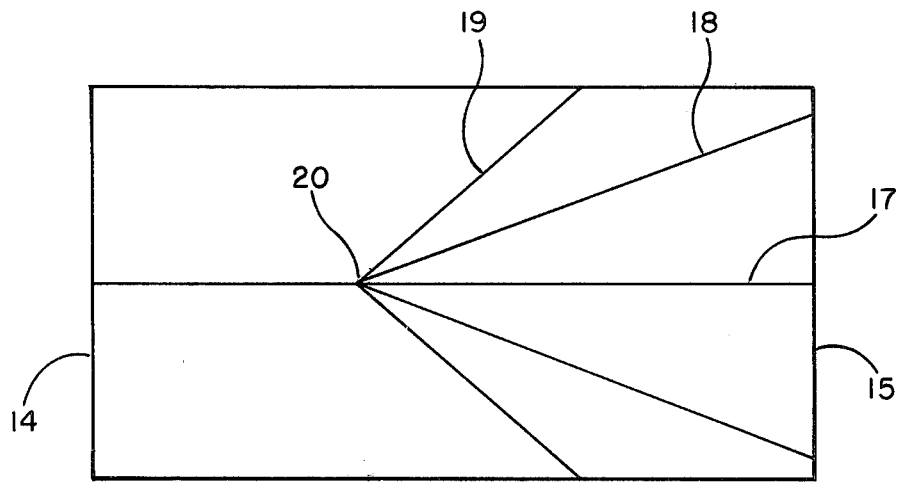
FIG. 15 is a schematic plan view showing still another arrangement of fold lines.
Figure 16:
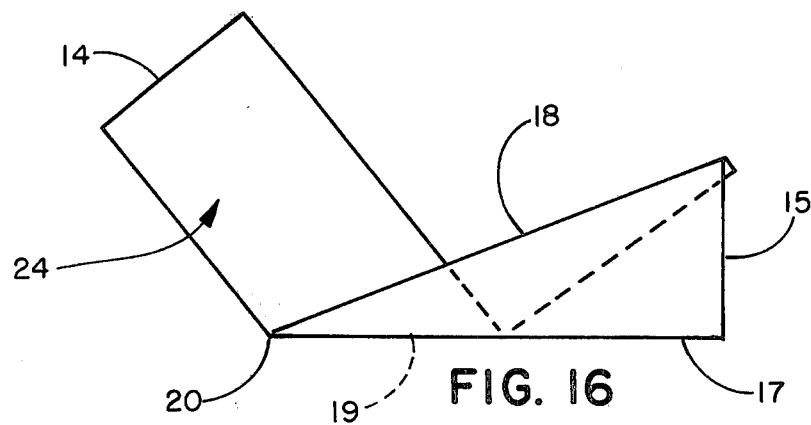
FIG. 16 is a side view of the FIG. 15 embodiment after folding.

Another variation may be obtained by adjusting the length of the anterior panel. As shown in FIGS. 15-16, as base point 20 is spaced farther inward from front edge 14, the anterior panel becomes greater in depth as measured from the front edge 14 and when placed in position on the body is capable of covering more and more of the abdomen as well as completely covering the pubic area of the perineum. Such a structure is desirable for example when the device is used for infant or adult diapering.

As indicated in FIGS. 15-16, when base point 20 is moved rearwardly to create a larger anterior panel without changing other sheet dimensions, the first set of rearwardly diverging lines 18 may intersect the periphery of the sheet at back edge 15 rather than at side edges 16. A variation of this type does not change the broad functionality of the device and may be desirable where shorter structures are useful such as in the previously mentioned dribble cups adapted to receive and contain small dribbles, weeping, involuntary dripping or the like.

The protective device of this invention may be made available in either flat or pre-folded condition. When provided in flat condition, the fold lines should be permanently scored, embossed or indented to facilitate folding as the device is being readied for use. After folding adhesive tape, adhesive spots or other securement means may be applied between folded panels, or at overlapping edges to aid in retaining the folded condition.

Preferably the sheet material is prefolded for convenience to the user. In such event, and as indicated above, it is preferably secured in its folded configuration by adhesive means such as dots 13 as shown in FIGS. 11 and 12, or by some other suitable securement means such as double faced tape, stitching, stapling or the like.

As previously mentioned, the device of this invention may be provided with its own suspension means rather than relying on a snug-fitting supporting garment or the like.

Figure 17:
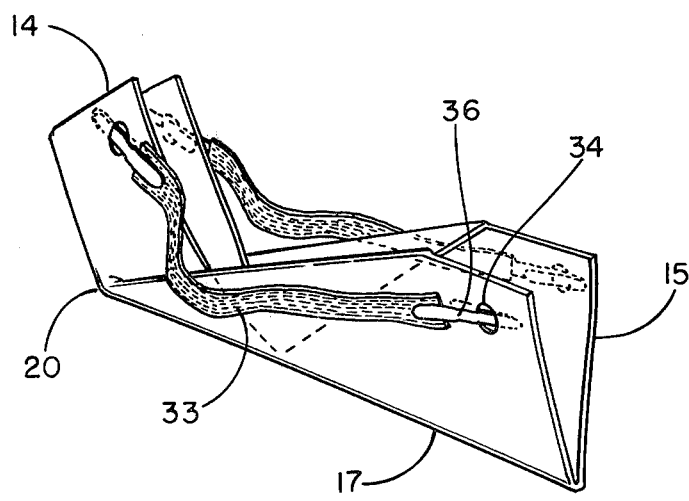
FIG. 17 is a side perspective view of the folded sheet material of FIG. 5 with a suspension means associated therewith.

An embodiment utilizing such suspension means is shown in FIG. 17. The suspension means shown there is in the form of a pair of flat tapes 33, preferably elastic, each of which extends from a front corner to a rear corner. In use, these tapes are designed to encircle the thighs. The tape may also be permanently secured to front and rear corner areas in which case each device has its own suspension means. In a preferred form, as shown in the drawing, the device may be provided with apertures 34, or buttonholes, disposed in each corner area and tape 33 may be provided with cooperating attachment means 36 secured to each end. In the embodiment shown, the cooperating attachment means 36 is in the form of flat hook elements of plastic or the like which slide into apertures 34 in releasable and rotatable fashion. With such an arrangement, one set of tapes may be used over and over again while the individual folded device is discarded after a single use.

Figure 18:
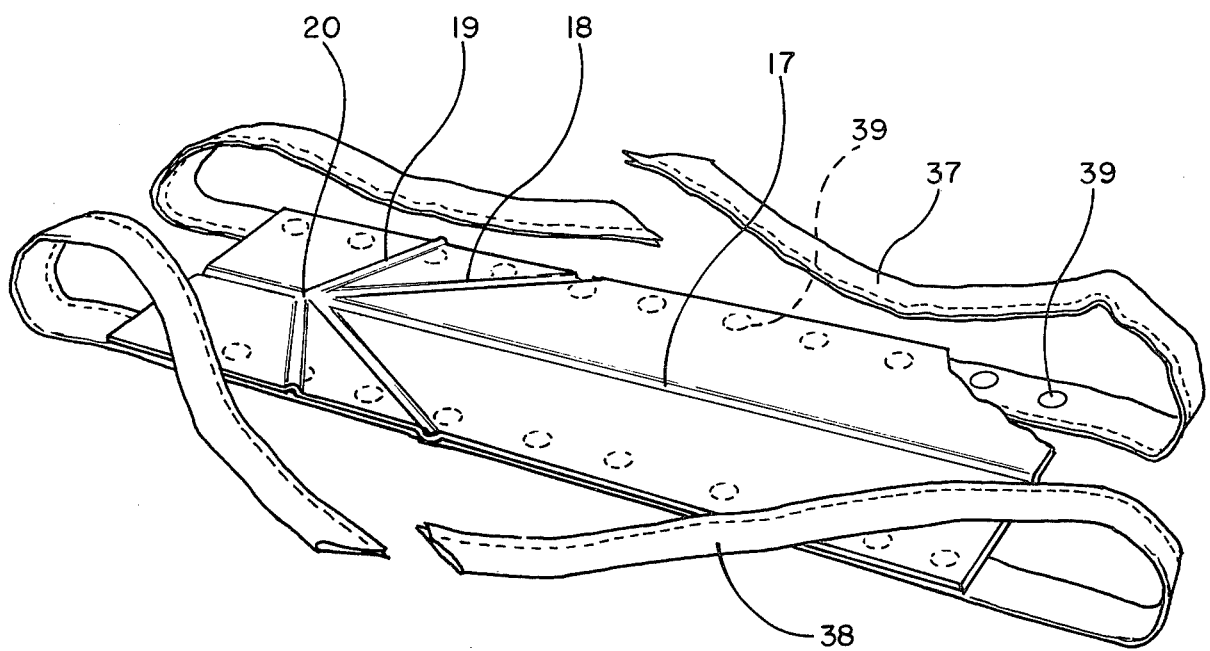
FIG. 18 is a top perspective view, partly cut away, of another embodiment of the sheet material of the invention having tie-straps incorporated therewith.
Figure 19:
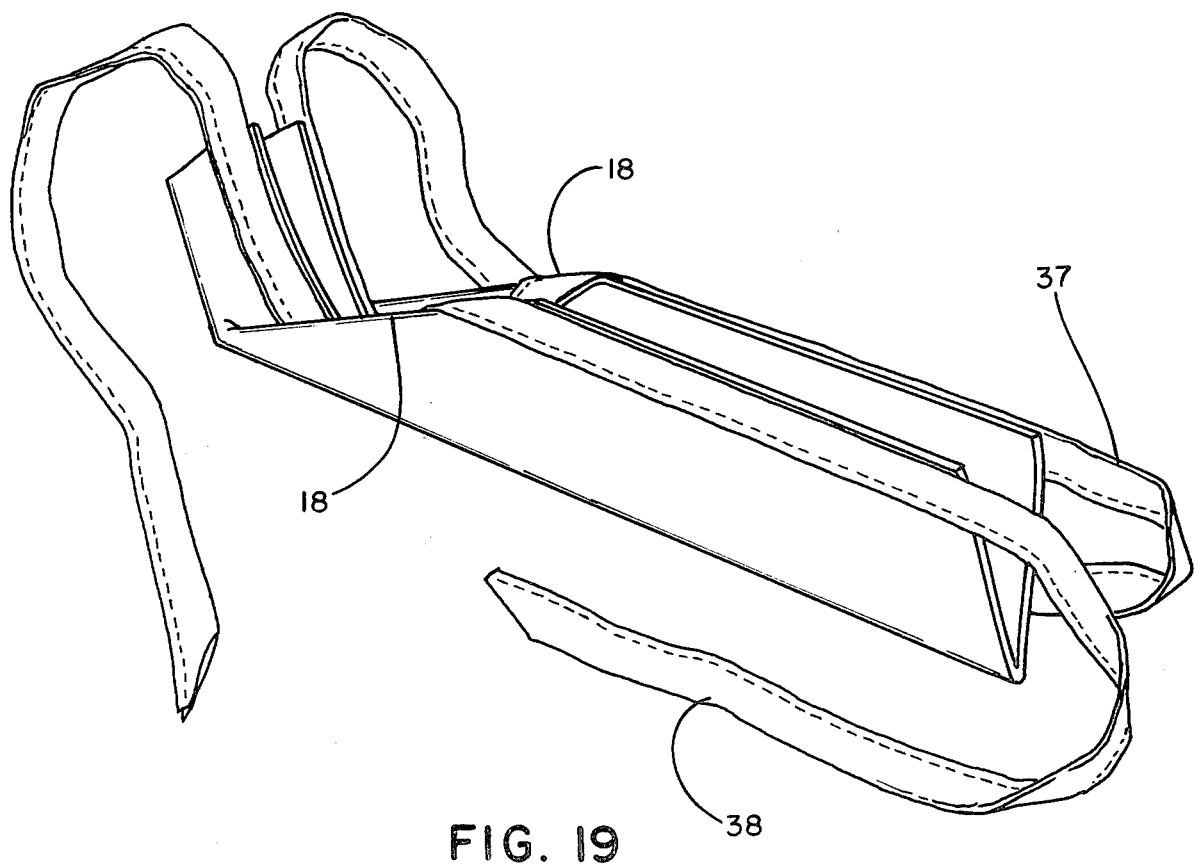
FIG. 19 is a side perspective view of the FIG. 18 embodiment after folding on the pre-established fold lines.

Another embodiment of the invention with its own suspension means is shown in FIGS. 18 and 19.

In FIG. 19 the sheet material with pre-established fold lines 17, 18 and 19 radiating from common apex 20 has a pair of straps 37 and 38 secured along each of the side edges with free ends extending beyond each end of the sheet. The free ends of the straps are intended to serve as ties for securing the containment device about the body. In the embodiment shown the straps 37 and 38 are secured to the sheet edges by means of spaced adhesive dots 39 as indicated in the cut-away portion of the drawing. While the spaced areas of securement are desirable because they preserve flexibility of the material, other securement means such as continuous adhesive lines, stitching, stapling or the like may be used.

In FIG. 19, the FIG. 18 embodiment is shown in its folded form. As indicated there, the straps are secured by lines of stitches.

The embodiment shown in FIGS. 18 and 19 is especially useful when the device is made in a large size suitable for incontinent pad or similar use.

For some uses, as in the protection of garments from the staining which might otherwise be caused by light discharge, the device may comprise a single layer of material, and the material may be either absorbent or non-absorbent. When discharge is expected to be light, it may, for example, be comprised of a thin sheet of plastic film such as polyethylene, vinyl or the like which would serve primarily to shield but not absorb. However, for comfort the film may be coated with a thin fiber layer on the top surface which could also be absorbent.

For use as a drip catcher or dribble cup, the sheet material can be made of a thin plastic sheet with a thin layer or layers of absorbent material laminated to the top surface. Creped cellulose wadding tissues, non-woven webs, or thin air-formed and bonded batts are suitable for this purpose. Such structure is also suitable for menstrual use during light flow, or in conjunction with tampons, or for use in garment protection when a hemorrhoidal condition exists.

For menstrual use during normal or heavy flow, the sheet material may comprise a bottom fluid impermeable sheet, a central core of absorbent material of any desired thickness depending upon the absorbent capacity needed, and a thin top layer of fluid permeable material such as one of the non-woven fiber webs now in common use on catamenial pads. The top fluid permeable layer may be made of hydrophobic or hydrophilic fibers.

A similar multilayered structure is also suitable when the device is designed for diapering uses. The only major difference in the latter structure as compared to catamenial pads being the size of the starting sheet.

For general comfort purposes the width of the sheet is preferably in the range of 2 to 8 inches, the length of the pad being varied to accommodate the particular end use. However, greater widths may be used without seriously hampering the functionality.

Catamenial napkins, for example, may comprise a flat sheet size ranging from about 2" to 4" to about 6"×10".

Infant diapers may range in size from about 8"×12" for newborns to about 8"–14"×20" for toddler's.

Geriatric diapers or adult incontinent garments may range in size from 8"–14"×20" to about 8"–18"×24".

The diapers may be used with a supporting garment to hold it in place or they may be made self-supporting and may be used without a supplementary garment by adding pressure-sensitive tapes at the corners of one end, or by using pins or other fastening means, to secure the diaper around the waist.

It has been found that when used with snug-fitting garments such as panties or pantyhose of stretch material that catamenial napkins made in accordance with this invention usually will need no additional securement means to remain comfortably in place. However, areas of pressure sensitive adhesive may be provided on the bottom side for securement if the supporting garment is not considered snug enough. Pressure sensitive adhesive may alternatively be provided on the top surface near the front and back edges for direct securement to the body.

While the preferred embodiments and specific examples depicted in the drawing show only an elongate rectilinear structure it is understood that the basic sheet material need not have a perimeter comprises of straight lines. The folded structure is equally applicable to sheet material with rounded corners and curved edges, and the terms generally elongate or generally rectangular are intended to include such forms.

What is claimed is:

1. A perineal shield and discharge containment device comprised of a sheet of flexible material in generally elongate form defined by a top body-contacting surface, a bottom surface, a front edge, a back edge and two side edges; said sheet being provided with a plurality of pre-established fold lines along which said sheet is folded prior to use;

said lines comprising:
(a) a main fold line centrally and longitudinally disposed on said sheet and extending the full length of said sheet,
(b) a first pair of rearwardly diverging fold lines originating on said main fold line at a common point spaced from the front edge of said sheet, and said diverging fold lines extending from said point to the perimeter of said sheet,
(c) a second pair of rearwardly diverging fold lines disposed between said first pair of diverging lines and the side edges of said sheet, said second pair of lines also originating at said point on said main fold line and extending from said point to the perimeter of said sheet;

said sheet being adapted for inward folding on said main fold line, inward folding on said first pair of rearwardly diverging fold lines, and outward folding on said second pair of rearwardly diverging fold lines.

2. The device of claim 1 wherein said sheet comprises a single layer of material.

3. The device of claim 1 wherein said sheet comprises a single layer of material consisting of a fluid impervious film.

4. The device of claim 1 wherein said sheet material comprises multilayered material.

5. The device of claim 1 wherein said sheet comprises two-layered material in which the top body-contacting surface layer is soft and fluid absorbent and the bottom surface layer is a fluid impervious film.

6. The device of claim 1 wherein said sheet comprises a three-layered material in which the top body-contacting surface layer is fluid pervious, the intermediate layer comprises a batt of absorbent material, and the bottom surface layer is a fluid impervious sheet material.

7. The device of claim 1 wherein said sheet is pre-folded along the defined fold lines.

8. The device of claim 1 wherein said device is pre-folded along the defined fold lines and is secured in folded condition by securement means disposed adjacent said second pair of rearwardly diverging folds.

9. The device of claim 2 wherein said sheet is pre-folded along the defined fold lines.

10. The device of claim 2 wherein said device is pre-folded along the defined fold lines and is secured in folded condition by securement means disposed adjacent said second pair of rearwardly diverging folds.

11. The device of claim 3 wherein said sheet is pre-folded along the defined fold lines.

12. The device of claim 3 wherein said device is pre-folded along the defined fold lines and is secured in folded condition by securement means disposed adjacent said second pair of rearwardly diverging folds.

13. The device of claim 5 wherein said sheet is pre-folded along the defined fold lines.

14. The device of claim 5 wherein said device is pre-folded along the defined fold lines and is secured in folded condition by securement means disposed adjacent said second pair of rearwardly diverging folds.

15. The device of claim 6 wherein said sheet is pre-folded along the defined fold lines.

16. The device of claim 6 wherein said device is pre-folded along the defined fold lines and is secured by securement means disposed adjacent said second pair of rearwardly diverging folds.

17. The device of claim 6 wherein said device is a sanitary napkin.

18. The device of claim 6 wherein said device is a baby diaper.

19. The device of claim 6 wherein said device is an adult incontinent garment.

20. The device of claim 15 wherein said device is a sanitary napkin.

21. The device of claim 15 wherein said device is a baby diaper.

22. The device of claim 15 wherein said device is an adult incontinent garment.

23. The device of claim 16 wherein said device is a sanitary napkin.

24. The device of claim 16 wherein said device is a baby diaper.

25. The device of claim 16 wherein said device is an adult incontinent garment.

26. The device of claim 1 wherein said device is provided with suspension means.

27. The device of claim 26 wherein said suspension means comprises a pair of flat tapes one each of said tapes extending along a side of said device with the free ends of each tape secured to the respective front and rear corner of said device.

28. The device of claim 27 in which the ends of said tape are provided with detachable means for releasable securement to said device.

29. The device of claim 27 in which said tapes are elastic.

30. The device of claim 26 wherein said suspension means comprises a pair of straps one each of said straps being secured along one edge of said device, each of said straps having free ends extending beyond the ends of said device to serve as tie means.

* * * * *